United States Patent
Odamaki et al.

(10) Patent No.: US 12,110,486 B2
(45) Date of Patent: *Oct. 8, 2024

(54) BIFIDOBACTERIUM BACTERIA AND COMPOSITION INCLUDING NOVEL BIFIDOBACTERIUM BACTERIA

(71) Applicant: MORINAGA MILK INDUSTRY CO., LTD., Tokyo (JP)

(72) Inventors: Toshitaka Odamaki, Kanagawa (JP); Kumiko Kato, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/146,706

(22) Filed: Dec. 27, 2022

(65) Prior Publication Data
US 2023/0137618 A1    May 4, 2023

Related U.S. Application Data

(62) Division of application No. 16/769,781, filed as application No. PCT/JP2018/045167 on Dec. 7, 2018, now Pat. No. 11,566,219.

(30) Foreign Application Priority Data

Dec. 8, 2017 (JP) ................. 2017-235892

(51) Int. Cl.
| | |
|---|---|
| C12N 1/20 | (2006.01) |
| A23L 2/52 | (2006.01) |
| A23L 33/00 | (2016.01) |
| A23L 33/125 | (2016.01) |
| A23L 33/135 | (2016.01) |
| A61K 35/745 | (2015.01) |
| A61K 47/26 | (2006.01) |
| A61K 47/36 | (2006.01) |
| A61K 35/00 | (2006.01) |

(52) U.S. Cl.
CPC ............. *C12N 1/20* (2013.01); *A23L 2/52* (2013.01); *A23L 33/125* (2016.08); *A23L 33/135* (2016.08); *A23L 33/40* (2016.08); *A61K 35/745* (2013.01); *A61K 47/26* (2013.01); *A61K 47/36* (2013.01); *A23V 2002/00* (2013.01); *A23V 2400/533* (2023.08); *A61K 2035/115* (2013.01)

(58) Field of Classification Search
CPC ....................................................... C12N 1/20
See application file for complete search history.

(56) References Cited

U.S. PATENT DOCUMENTS

2021/0139842 A1   5/2021   Odamaki et al.

FOREIGN PATENT DOCUMENTS

| EP | 3181683 A1 | 6/2017 |
|---|---|---|
| JP | 2014-094001 A | 5/2014 |
| WO | WO2012/156898 A1 | 11/2012 |
| WO | WO2016/175702 A1 | 11/2016 |

OTHER PUBLICATIONS

Office Action from China National Intellectual Property Administration for Application No. 2018-80079393 (Mar. 1, 2023) with English translation.
Liu, Songling et al., "Starch and starch hydrolysates are favorable carbon sources for Bifidobacteria in the human gut," BMC Microbiology (2015);15:54; pp. 1-9.
Yu, Z.-T., et al., Utilization of major fucosylated and sialylated human milk oligosaccharides by isolated human gut microbes,: Glycobiol. 2013;23(11):1281-1292.
Garrido, D., et al., "A novel gene cluster allows preferential utilization of fucosylated milk oligosaccharides in *Bifidobacterium longum* subsp. *longum* SC596," Scientific Reports, 2016, vol. 6, 35045 (18 pp.).
Riviere, A., et al., "The Ability of Bifidobacteria to Degrade Arabinoxylan Oligosaccharide Constituents and Derived Oligosaccharides Is Strain Dependent," Appl. Environmen. Microbiol. 2014;80(1):204-217.
Gavlighi, H. A., et al., "Enzymatic Depolymerization of Gum Tragacanth: Bifidogenic Potential of Low Molecular Weight Oligosaccharides," J. Agricultural Food Chem. 2013;61:1272-1278.
Matsuki, T., et al., "A key genetic factor for fucosyllactose utilization affects infant gut microbiota development," Nature Communications 2016; 7:11939; DOI:10.1038/ncomms11939; pp. 1-12.

(Continued)

*Primary Examiner* — Rosanne Kosson
(74) *Attorney, Agent, or Firm* — Cermak & McGowan LLP; Shelly Guest Cermak

(57) ABSTRACT

Provide are beneficial bacteria that can be beneficially applied across a wide range of age groups and a composition containing the same. *Bifidobacterium longum* subspecies *longum* NITE BP-02568 and/or *Bifidobacterium longum* subspecies *longum* NITE BP-02569; and *Bifidobacterium longum* subspecies *longum*, having utilization ability for 2'-fucosyllactose are also provided. More preferably, bacteria having utilization ability for carbohydrates arabinoxylan, arabinan, and pectic galactan; and a composition containing the bacteria are also provided. More preferably, a composition containing 2'-fucosyllactose are also provided. More preferably, a composition containing at least one carbohydrate selected from the group consisting of arabinoxylan, arabinan, pectic galactan, and oligosaccharides derived therefrom or containing at least a carbohydrate derived from a gramineous plant or a carbohydrate derived from a solanaceous plant are also provided.

3 Claims, No Drawings

Specification includes a Sequence Listing.

(56) References Cited

OTHER PUBLICATIONS

The Intestinal Microbiology Society (IMS)/formerly Japan Bifidus Foundation (JBF), Japan Bifidus Foundation (JBF)/Intestinal Microbiology, 2019, downloaded Feb. 21, 2020, https://bifidus-fund.jp/en/index.shtml, pp. 1-4.

Urashima, T., et al., "Biological significance of human milk oligosaccharides," Milk Science 2008;56(4):22 pp.

International Search Report for PCT Patent App. No. PCT/JP2018/045167 (Mar. 5, 2019).

Extended European Search Report for European Patent App. No. 18885298.2 (Oct. 20, 2021).

Yue, K., "Human milk oligosaccharides (HMOs) and their effects on intestinal microorganisms," Inaugural-Dissertation zur Erlangung des Doktorgrades (Dr. oec. troph.) im Fachbereich Agrarwissenschaften, Oekotrophologie und Umweltmanagement der Justus-Liebig-Universitaet Giessen, 2015, pp. 1-134, retrieved from Internet, URL: http://geb.uni-giessen.de/geb/volltexte/2015/11821/pdf/YueKe_2015_11_03.pdf.

Liu, S., et al., "Starch and starch hydrolysates are favorable carbon sources for Bifidobacteria in the human gut," BMC Microbiol. 2015;15(54):9 pp.

SEQUENCE LISTING

```
Sequence total quantity: 2
SEQ ID NO: 1            moltype = DNA   length = 1535
FEATURE                 Location/Qualifiers
source                  1..1535
                        mol_type = genomic DNA
                        organism = Bifidobacterium longum
SEQUENCE: 1
tttttgtgga gggttcgatt ctggctcagg atgaacgctg gcggcgtgct taacacatgc   60
aagtcgaacg ggatccatca agcttgcttg gtggtgagag tggcgaacgg gtgagtaatg  120
cgtgaccgac ctgccccata caccggaata gctcctggaa acgggtggta atgccggatg  180
ctccagttga tcgcatggtc ttctgggaaa gctttcgcgg tatgggatgg ggtcgcgtcc  240
tatcagcttg acggcggggt aacggcccac cgtggcttcg acgggtagcc ggcctgagag  300
ggcgaccggc cacattggga ctgagatacg gcccagactc ctacgggagg cagcagtggg  360
gaatattgca caatgggcgc aagcctgatg cagcgacgcc gcgtgaggga tggaggcctt  420
cgggttgtaa acctctttta tcggggagca agcgagagtg agtttacccg ttgaataagc  480
accggctaac tacgtgccag cagccgcggt aatacgtagg gtgcaagcgt tatccggaat  540
tattgggcgt aaagggctcg taggcggttc gtcgcgtccg gtgtgaaagt ccatcgctta  600
acggtggatc cgcgccgggt acgggcgggc ttgagtgcgg tagggagac tggaattccc  660
ggtgtaacgg tggaatgtgt agatatcggg aagaacacca atggcgaagg caggtctctg  720
ggccgttact gacgctgagg agcgaaagcg tggggagcga acaggattag atacctggt  780
agtccacgcc gtaaacggtg gatgctggat gtggggcccg ttccacgggt tccgtgtcgg  840
agctaacgcg ttaagcatcc cgcctgggga gtacggccgc aaggctaaaa ctcaaagaaa  900
ttgacggggg cccgcacaag cggcggagca tgcggattaa ttcgatgcaa cgcgaagaac  960
cttacctggg cttgacatgt tcccgacggt cgtagagata cggcttccct tcggggcggg 1020
ttcacaggtg gtgcatggtc gtcgtcagct cgtgtcgtga gatgttgggt taagtcccgc 1080
aacgagcgca accctcgccc cgtgttgcca gcggattatg ccgggaactc acggggggacc 1140
```

```
gccggggtta actcggagga aggtggggat gacgtcagat catcatgccc cttacgtcca 1200
gggcttcacg catgctacaa tggccggtac aacgggatgc gacgcggcga cgcggagcgg 1260
atccctgaaa accggtctca gttcggatcg cagtctgcaa ctcgactgcg tgaaggcgga 1320
gtcgctagta atcgcgaatc agcaacgtcg cggtgaatgc gttcccgggc cttgtacaca 1380
ccgcccgtca agtcatgaaa gtgggcagca cccgaagccg gtggcctaac cccttgtggg 1440
atggagccgt ctaaggtgag gctcgtgatt gggactaagt cgtaacaagg tagccgtacc 1500
ggaaggtgcg gctggatcac ctcctttcta cggag                            1535

SEQ ID NO: 2              moltype = DNA   length = 1536
FEATURE                   Location/Qualifiers
source                    1..1536
                          mol_type = genomic DNA
                          organism = Bifidobacterium longum
SEQUENCE: 2
tttttgtgga gggttcgatt ctggctcagg atgaacgctg gcggcgtgct taacacatgc  60
aagtcgaacg ggatccaccg ggctttgctt ggtggtgaga gtggcgaacg ggtgagtaat 120
gcgtgaccga cctgccccat acaccggaat agctcctgga aacgggtggt aatgccggat 180
gctccagttg atcgcatggt cttctgggaa agctttcgcg gtatgggatg gggtcgcgtc 240
ctatcagctt gacggcgggg taacggccca ccgtggcttc gacgggtagc cggcctgaga 300
gggcgaccgg ccacattggg actgagatac ggcccagact cctacgggag gcagcagtgg 360
ggaatattgc acaatgggcg caagcctgat gcagcgacgc cgcgtgaggg atggaggcct 420
tcgggttgta aacctctttt atcggggagc aagcgagagt gagtttaccc gttgaataag 480
caccggctaa ctacgtgcca gcagccgcgg taatacgtag ggtgcaagcg ttatccggaa 540
ttattgggcg taaagggctc gtaggcggtt cgtcgcgtcc ggtgtgaaag tccatcgctt 600
aacggtggat ccgcgccggg tacggcgggc ttgagtgcg gtaggggaga ctggaattcc 660
cggtgtaacg gtggaatgtg tagatatcgg gaagaacacc aatgcgaag gcaggtctct 720
gggccgttac tgacgctgag gagcgaaagc gtggggagcg aacaggatta gataccctgg 780
tagtccacgc cgtaaacggt ggatgctgga tgtggggccc gttccacggg ttccgtgtcg 840
gagctaacgc gttaagcatc ccgcctgggg agtacggccg caaggctaaa actcaaagaa 900
attgacgggg gcccgcacaa gcggcggagc atgcggatta attcgatgca acgcgaagaa 960
ccttacctgg gcttgacatg ttcccgacgg tcgtagagat acggcttccc ttcggggcgg 1020
gttcacaggt ggtgcatggt cgtcgtcagc tcgtgtcgtg agatgttggg ttaagtcccg 1080
caacgagcgc aaccctcgcc ccgtgttgcc agcggattat gccgggaact cacggggac 1140
cgccggggtt aactcggagg aaggtgggga tgacgtcaga tcatcatgcc ccttacgtcc 1200
agggcttcac gcatgctaca atggccggta caacgggatg cgacgcggca acgcggagcg 1260
gatccctgaa aaccggtctc agttcggatc gcagtctgca actcgactgc gtgaaggcgg 1320
agtcgctagt aatcgcgaat cagcaacgtc gcggtgaatg cgttcccggg ccttgtacac 1380
accgcccgtc aagtcatgaa agtgggcagc acccgaagcc ggtggcctaa cccccttgtgg 1440
gatggagccg tctaaggtga ggctcgtgat tgggactaag tcgtaacaag gtagccgtac 1500
cggaaggtgc ggctggatca cctcctttct acggag                          1536
```

BIFIDOBACTERIUM BACTERIA AND COMPOSITION INCLUDING NOVEL BIFIDOBACTERIUM BACTERIA

This application is a Divisional application under 35 U.S.C. § 120 of U.S. patent application Ser. No. 16/769,781, filed Jun. 4, 2020, which was a national phase entry under 35 U.S.C. § 371 of PCT Patent Application No. PCT/JP2018/045167, filed on Dec. 7, 2018, which claims priority under 35 U.S.C. § 119 to Japanese Patent Application No. 2017-235892, filed Dec. 8, 2017, both of which are incorporated by reference. Also, the Sequence Listing filed electronically herewith is hereby incorporated by reference (File name: 2022-12-27T_216-030D_SEQ_LIST.xml; File size: 6 KB; Date recorded: Dec. 27, 2022).

TECHNICAL FIELD

The present invention relates to novel *Bifidobacterium*, a composition includingthe bacteria, and a composition for promoting the growth of the bacteria.

BACKGROUND ART

In recent years, there has been a surge of research on probiotics, in which microorganisms with beneficial effects on animals (beneficial bacteria) are actively ingested to regulate the intestinal environment, thereby suppressing the onset of diseases and promoting the health. Probiotics can also be used in conjunction with prebiotics, which help the growth of beneficial bacteria. "Probiotics" refers to bacteria that beneficially work in the intestine, while "prebiotics" refers to substances that serve as selective nutrient sources for such beneficial bacteria and promote their growth. It is known that prebiotics have beneficial effects on human health, such as lactic acid bacteria/bifidobacteria growth promoting action, intestinal regulation action, and preventing/alleviating action against inflammatory bowel diseases.

For example, Patent Document 1 discloses a lactic acid bacteria growth promoter characterized by having an average molecular weight of 10,000 to 300,000 and containing an agar with the reducing sugar amount adjusted to 0.12 to 2.0.

Thus, intensive research has been conducted on probiotics and prebiotics.

CITATION LIST

Patent Document

PTL 1: JP-A-2014-94001

SUMMARY OF INVENTION

Technical Problem

It is generally known that the intestinal flora in babies and infants, and the intestinal bacterial flora in adults, are different, and the kind of beneficial bacteria and their proportion are also different between the two. For this reason, it is desired that excellent probiotic effects are obtained both in babies and infants and in adults by administering intestinal beneficial bacteria or administering a component that helps the growth of intestinal beneficial bacteria.

However, beneficial bacteria abundantly present in the intestines of babies and infants are often adapted to the nutrients of human milk and cannot apply components derived from adult meals (dietary fibers, etc.). Thus, even if one who has become an adult actively ingests such diminishing beneficial bacteria, it is difficult for the bacteria to grow in the intestine. In addition, even if beneficial bacteria that grow well in the adult meal environment are actively ingested by babies and infants, it often happens that the expected effects on babies and infants, such as formation of intestinal bacterial flora, digestion and absorption of human milk, protection against infection, etc. are not often obtained.

Like this, difficulties lie in the approach to providing beneficial bacteria that easily grow in the intestine and can be beneficially applied across a wide range of age groups including babies, infants, and adults; and a composition containing the same.

Thus, a main object of the present technology is to provide beneficial bacteria that can be beneficially applied across a wide range of age groups, and also a composition containing the same.

Solution to Problem

The present inventors, when trying to obtain beneficial bacteria that can be used beneficially in a wide range of ages for both infants and adults, first examined the differences in their dietary habits.

Then, as a result of intensive research, the present inventors have found that in *Bifidobacterium longum* subspecies *longum* (hereinafter also referred to as subspecies longum) collected from human intestinal bacteria, there exists a novel bacterial group whose properties are different from the properties of the conventionally known subspecies longum.

Specifically, completely by chance, the present inventors have found that there exists a novel bacterial group of *Bifidobacterium longum* subspecies *longum* having utilization ability for 2'-fucosyllactose.

Reference 1 (Nature Communications, 7:11939, pp. 1-12, (2016) 6, Volume 80, Number 14 (2014)) describes that the key genetic factor for utilization of fucosyllactose affects the development of the intestinal flora in babies and infants. As described in Table 1 of Reference 1, it has been shown that with respect to all the six types of *Bifidobacterium longum* subspecies *longum*, the growth is hardly observed on human milk oligosaccharides (−) or human milk oligosaccharides, and that they do not have the properties of α-L-fucosidase (−) or α-L-fucosidase.

However, the above bacteria is capable of utilizing 2'-fucosyllactose, which is abundantly present in human milk oligosaccharides and is a typical oligosaccharide. Generally, *Bifidobacterium* inhabiting in adults and *Bifidobacterium* not inhabiting in humans can not apply human milk oligosaccharides. For this reason, because the above bacteria is capable of applying human milk oligosaccharides (HMOs) ingested by babies and infants, such bacteria can easily grow in the intestines of babies and infants.

Further, they have also found that some bacteria in this group are capable of utilizing at least one carbohydrate of "arabinoxylan, debranched arabinan, and pectic galactan". Such a bacteria utilizes a carbohydrate resulting from partial digestion of eaten gramineous plants or solanaceous plants, which are staple foods for adults, by gastric acid or the like, and thus easily grows also in the intestines of humans who have eaten them.

As described above, the novel bacterial group found by the present inventors easily grows in the intestines of babies and infants and further, if necessary, easily grows also on foods eaten by adults (e.g., Japanese dishes), and thus is applicable across a wide range of age groups. This bacterial group can also contribute to excellent intestinal flora formation across a wide range of age groups including both infants and adults.

Incidentally, "Japanese dishes" as used herein refers to a meal in which the staple food is rice (particularly boiled rice or rice gruel). Further, the meal desirably contains, as main or side dishes, root vegetable dishes (e.g., potatoes, etc.); or legume dishes (e.g., tofu (soybean curd), fermented soybean products (e.g., miso (soybean paste), natto (fermented soybeans), etc.), etc.).

Therefore, the present inventors have found beneficial bacteria that can be beneficially applied across a wide range of age groups including infants and adults, and that the beneficial bacteria area novel bacterial group, that is, subspecies *longum* of *Bifidobacterium longum* having utilization ability for 2'-fucosyllactose; and also found that a composition containing the beneficial bacteria and a composition for promoting the growth of the beneficial bacteria can be newly provided.

That is, the invention is as follows.

[1] *Bifidobacterium longum* subspecies *longum* NITE BP-02568 and/or *Bifidobacterium longum* subspecies *longum* NITE BP-02569.

[2] *Bifidobacterium longum* subspecies *longum*, having utilization ability for 2'-fucosyllactose.

[3] The bacteria according to the above [2], further having utilization ability for at least one carbohydrate selected from the group consisting of arabinoxylan, arabinan, and pectic galactan.

[4] The bacteria according to the above [2] to [3], wherein the bacteria are *Bifidobacterium longum* subspecies *longum* NITE BP-02568 and/or *Bifidobacterium longum* subspecies *longum* NITE BP-02569.

[5] A composition containing the bacteria according to any one of the above [2] to [4].

[6] The composition according to the above [5], wherein the composition is a probiotic composition.

[7] The composition according to the above [5] to [6], wherein the composition is used at least for babies and infants, for adults, or for elderly people.

[8] The composition according to any one of the above [5] to [7], wherein the composition is used for intestinal regulation or for foods and beverages.

[9] The composition according to any one of the above [5] to [8], further containing 2'-fucosyllactose.

[10] The composition according to the above [9], further containing at least one carbohydrate selected from the group consisting of arabinoxylan, arabinan, pectic galactan, and oligosaccharides derived therefrom.

[11] The composition according to the above [9] or [10], further containing at least a carbohydrate derived from a gramineous plant or a carbohydrate derived from a solanaceous plant.

[12] A prebiotic composition for use in promoting the growth of *Bifidobacterium longum* subspecies *longum*, the composition containing 2'-fucosyllactose.

[13] The prebiotic composition according to the above [12], the composition further containing at least one carbohydrate selected from the group consisting of arabinoxylan, arabinan, pectic galactan, and oligosaccharides derived therefrom.

[14] A method for producing a composition containing microorganisms that are classified as *Bifidobacterium longum* subspecies *longum* and have utilization ability for 2'-fucosyllactose.

[15] The method according to the above [14], wherein the bacteria are *Bifidobacterium longum* subspecies *longum* NITE BP-02568 and/or *Bifidobacterium longum* subspecies *longum* NITE BP-02569.

[16] *Bifidobacterium longum* subspecies *longum* NITE BP-02568 and/or *Bifidobacterium longum* subspecies *longum* NITE BP-02569 for use in a composition.

[17] Use of *Bifidobacterium longum* subspecies *longum* NITE BP-02568 and/or *Bifidobacterium longum* subspecies *longum* NITE BP-02569 in producing a composition.

[18] A method for preventing, alleviating, or treating allergic symptoms, immune dysfunction, infectious diseases, or nervous system diseases by probiotics, the method including administering *Bifidobacterium longum* subspecies *longum* NITE BP-02568 and/or *Bifidobacterium longum* subspecies *longum* NITE BP-02569.

Advantageous Effects of Invention

According to the present technology, beneficial bacteria that can be beneficially applied in a wide range of age groups, a composition containing the same, and a composition for promoting the growth of the beneficial bacteria can be provided. Incidentally, the effects are not necessarily limited to those described herein and may be any of the effects described in the present technology.

DESCRIPTION OF EMBODIMENTS

Next, preferred embodiments of the invention will be described. Note that the invention is not limited to the following preferred embodiments, and can be freely modified within the scope of the invention. Incidentally, unless otherwise noted, percentages herein are by mass.

<Novel *Bifidobacterium*>

The present technology is novel *Bifidobacterium*. The bacteria are microorganisms classified as of *Bifidobacterium longum* subspecies *longum* (*Bifidobacterium longum* subspecies *longum*), and are a novel bacterial group having the unprecedented, extremely unique characteristics as described above, that is, having utilization ability for "2'-fucosyllactose" (hereinafter sometimes referred to as "subspecies *longum* of the present technology").

Because of this utilization ability, the subspecies *longum* of the present technology can easily grow on a composition containing 2'-fucosyllactose (e.g., human milk, human milk oligosaccharides (HMOs), powdered milks, etc.). As a result of using 2'-fucosyllactose, the growth of the subspecies *longum* of the present technology in the intestine is also facilitated.

Incidentally, the details of the components of the "2'-fucosyllactose" will be described below in the "component (a): 2'-fucosyllactose".

*Bifidobacterium* have been reported to have various physiological functions, and it has also been reported that such functions are due to growth in the intestine or substances produced (e.g., acetic acid, etc.).

Therefore, the subspecies *longum* of the present technology can also be expected to be highly safe and have the generally supposed efficacy of *Bifidobacterium* in a wide range of age groups. For this reason, the subspecies *longum* of the present technology can be used for a wide range of compositions (for foods and beverages, for functional foods, for pharmaceuticals, for animal feeds, etc.).

In addition, the subspecies *longum* of the present technology can be expected to have probiotic effects, and thus can also be used for the purposes of health promotion, diet improvement, intestinal environment improvement, intestinal infection prevention/treatment, and the like.

In addition, as probiotic effects, alleviating action on constipation and diarrhea, alleviating action on lactose intolerance, immune function improving action, protecting action against infection, allergy suppressing action, preventing action on arteriosclerosis, antitumor action, and the like are known (Reference 2: bifidus-fund.jp/en/index.shtml). In addition, human milk oligosaccharides are known to have, for example, preventing action on allergies, lactose intolerance alleviating action, immunity improving action, protecting action against infection, cerebral nervous system forming action, cerebral nervous system activating action, and like (Reference 3: Milk Science Vol. 56, No. 4 (2008) pp. 155-176).

The subspecies *longum* of the present technology can be expected to have probiotic effects and can also effectively apply human milk oligosaccharides. Therefore, for example, the prevention, alleviation, or treatment of diseases, symptoms, or conditions, such as allergic symptoms (e.g., allergic inflammation, atopic dermatitis, etc.), immune dysfunction (e.g., immune hypofunction, etc.), infectious diseases (e.g., viral gastroenteritis, bacterial infectious diseases, etc.), and nervous system diseases (e.g., neurological diseases of the brain, bone marrow, or the like, etc.), can be expected. In addition, the subspecies longum of the present technology can also be expected to have preventing/alleviating action on allergic symptoms, lactose intolerance alleviating action, immunity improving action, protecting action against infection, cerebral nervous system forming action, cerebral nervous system activating action, and the like.

It is preferable that the subspecies *longum* of the present technology is characterized by having utilization ability for at least one carbohydrate selected from the group consisting of arabinoxylan, arabinan, and pectic galactan. As the arabinan, debranched arabinan is preferable.

Incidentally, the details of the components of the "arabinoxylan, arabinan, and pectic galactan" will be described below in the "components (b)".

Unless otherwise noted, "carbohydrate" as used herein has a meaning including "polysaccharides" and "oligosaccharides" that the subspecies *longum* of the present technology can utilize. Oligosaccharides are those composed of about 2 to 10 sugar residues.

The subspecies *longum* of the present technology has utilization ability for at least one carbohydrate selected from the group consisting of "arabinoxylan, arabinan, and pectic galactan". As a result, the subspecies *longum* of the present technology can easily grow on a composition containing at least such a carbohydrate (e.g., processed staple foods (rice, wheat, corn, potatoes, etc.), etc.), and thus the growth in the intestine is facilitated.

In the case of growing the subspecies *longum* of the present technology, because the "arabinoxylan and arabinan" are known as carbohydrates present in gramineous plants, it is preferable to use a carbohydrate derived from a gramineous plant (preferably an oligosaccharide).

In addition, in the case of growing the subspecies *longum* of the present technology, because the "pectic galactan" is known as a carbohydrate present in solanaceous plants, it is preferable to use a carbohydrate derived from a solanaceous plant (preferably an oligosaccharide).

In addition, when gramineous plants (e.g., rice, wheat, corn, etc.) or solanaceous plants (e.g., potatoes, etc.), which are staple foods for adults, are eaten and partially digested, a carbohydrate arabinoxylan, arabinan, or pectic galactan is present therein. For this reason, the subspecies longum of the present technology capable of utilizing not only the "2'-fucosyllactose" but also at least one of the carbohydrates "arabinoxylan, arabinan, and pectic galactan" can easily grow in the intestine when a Japanese dish using rice, potatoes, or the like is eaten, and thus can be regarded as a further unique bacterial group of subspecies *longum*.

Further, with respect to the utilization ability, it is preferable that the subspecies *longum* of the present technology has high utilization ability for arabinoxylan and/or pectic galactan. More preferably, the subspecies longum of the present technology has high utilization ability for arabinoxylan and pectic galactan.

Examples of the subspecies *longum* of the present technology include *Bifidobacterium longum* subspecies *longum* NITE BP-02568 (accession No.: NITE BP-02568) and *Bifidobacterium longum* subspecies *longum* NITE BP-02569 (accession No.: NITE BP-02569). One or more kinds can be selected from these groups.

Incidentally, hereinafter, the *longum* NITE BP-02568 (accession No.: NITE BP-02568) is also referred to as "subspecies *longum* NITE BP-02568", and the longum NITE BP-02569 (accession No.: NITE BP-02569) is also referred to as "subspecies *longum* NITE BP-02569".

The subspecies *longum* NITE BP-02568 and subspecies *longum* NITE BP-02569 of the present technology are bacteria having high utilization ability for 2'-fucosyllactose, arabinoxylan, and pectic galactan, and thus are particularly preferable in the bacterial group of the subspecies *longum* of the present technology. The utilization abilities for 2'-fucosyllactose of these two strains are each OD 0.6 or more in the <Evaluation Method for Utilization of Saccharide Source> described below and are extremely excellent.

The subspecies *longum* NITE BP-02568 has SEQ ID NO: 1, and the subspecies *longum* NITE BP-02569 has SEQ ID NO: 2.

These two strains are classified as the novel bacterial group of subspecies *longum* internationally deposited at National Institute of Technology and Evaluation, NITE Patent Microorganisms Depositary (NPMD), as a *Bifidobacterium longum* MCLON2FL1 (accession No.: NITE BP-02568) strain and a *Bifidobacterium longum* MCLON2FL2 (accession No.: NITE BP-02569) strain.

The subspecies *longum* NITE BP-02568 of the present technology was, from the following mycological properties and characteristics, internationally deposited as a novel strain to National Institute of Technology and Evaluation, NITE Patent Microorganisms Depositary (NPMD), (address: 2-5-8 Kazusakamatari, Kisarazu, Chiba 292-0818, Japan) on Nov. 10, 2017, as a *Bifidobacterium longum* MCLON2FL1 (accession No.: NITE BP-02568) strain. This strain is available to the public from the above collection.

The subspecies *longum* NITE BP-02569 of the present technology was, from the following mycological properties and characteristics, internationally deposited as a novel strain to National Institute of Technology and Evaluation, NITE Patent Microorganisms Depositary (NPMD), (address: 2-5-8 Kazusakamatari, Kisarazu, Chiba 292-0818, Japan) on Nov. 10, 2017, as a *Bifidobacterium longum* MCLON2FL2 (accession No.: NITE BP-02569) strain. This strain is available to the public from the above collection.

The subspecies *longum* NITE BP-02568 and subspecies *longum* NITE BP-02569 of the present technology are not limited to the above deposited strains, and may also be strains substantially homogeneous to the deposited strains. "Substantially homogeneous strain" means a strain that is classified as subspecies *longum* of *Bifidobacterium longum* and at least has utilization ability for the "2'-fucosyllactose" equal to or higher than that of the subject deposited strain.

Further, a strain having sugar utilization ability for the "at least one member selected from the group consisting of arabinoxylan, arabinan, and pectic galactan" is preferable, and a strain having utilization ability for carbohydrates arabinoxylan and galactan is more preferable. In addition, a strain having, in addition to the 2'-fucosyllactose utilization ability, having utilization ability for lacto-N-tetraose is still more preferable.

In addition, a substantially homogeneous strain has a 16SrRNA gene base sequence 100% identical to the sequence of SEQ ID NO: 1 or SEQ ID NO: 2 of each strain (see Tables 2 and 3), and has the same mycological properties as the deposited strain. Further, unless the effects of the invention are impaired, the subspecies *longum* of the present technology may also be a strain bred from the subject deposited strain or a strain substantially homogeneous thereto by mutation, genetic recombination, selection of a naturally occurring mutant strain, or the like.

<Evaluation Method for Utilization of Saccharide Source>

Into 1 mL of an MRS (de Man-Rogosa-Sharpe) liquid medium containing a sugar source, strains are each inoculated at 1 v/v % and cultured at 37° C. under anaerobic conditions. The turbidity (OD 600) is measured after 24 hours of culture, and the difference after subtracting the turbidity of a control, in which a medium not inoculated with the strain is similarly cultured, is used to determine the presence of utilization and the degree of utilization ability according to the following standards. When the difference in OD 600 from the control is 0.3 or more, the strain is rated as "having excellent utilization", 0.5 or more as "having more excellent utilization", 0.6 or more as "having still more excellent utilization", and 0.8 or more as "having extremely excellent utilization".

The subspecies *longum* of the present technology can be grown, for example, by culturing the same strain.

The culturing method is not particularly limited as long as the subspecies *longum* of the present technology can grow, and a method commonly used for culturing *Bifidobacterium* can be suitably modified if necessary and used. For example, the culturing temperature may be 30 to 50° C., and is preferably 35 to 45° C. In addition, culture is preferably performed under anaerobic conditions. For example, the strain may be cultured while passing an anaerobic gas, such as carbon dioxide. In addition, culture under microaerophilic conditions, such as liquid stationary culture, is also possible.

The medium for growing the subspecies *longum* of the present technology is not particularly limited, and a medium commonly used for culturing *Bifidobacterium* can be suitably modified if necessary and used. That is, as carbon sources, in addition to the components (a) and (b) described below, for example, saccharides such as galactose, glucose, fructose, mannose, cellobiose, maltose, lactose, sucrose, trehalose, starch hydrolysates, and blackstrap molasses can be used according to the utilization. As nitrogen sources, for example, ammonium salts and nitrate salts, such as ammonia, ammonium sulfate, ammonium chloride, and ammonium nitrate, can be used. In addition, as inorganic salts, for example, sodium chloride, potassium chloride, potassium sulfate, magnesium sulfate, calcium chloride, calcium nitrate, manganese chloride, ferrous sulfate, and the like can be used. In addition, organic components such as peptone, soybean flour, defatted soybean cake, meat extracts, and yeast extracts may also be used. In addition, as a prepared medium, an MRS medium can be preferably used, for example.

As the subspecies *longum* of the present technology, the culture product obtained after culture may be directly used, or may also be diluted or concentrated and used. It is also possible to use bacterial cells recovered from the culture product. In addition, unless the effects of the invention are impaired, culture may be followed by various additional operations such as heating and lyophilizing. It is preferable that such an additional operation results in high survivability of viable cells.

Incidentally, the bacterial cells of the subspecies *longum* of the present technology for use in the pharmaceutical composition, food or beverage, or animal feed of the present technology are preferably viable cells.

Preferred examples of utilization components for the subspecies *longum* of the present technology include the following component (a) and/or components (b), and further the following components (c).

The "component (a): 2'-fucosyllactose" used in the present technology has growth promoting action on the subspecies *longum* of the present technology. Further, when the "component (a)" is combined with the "components (b)" and/or "components (c)" described below, the growth promoting action on the subspecies *longum* of the present technology can be more stably exerted. As a result, the growth of the subspecies *longum* of the present technology in the intestine is facilitated across a wide range of age groups. Further, in terms of the growth promoting action on the subspecies longum of the present technology, it is preferable that lacto-N-tetraose (LNT) is also a utilization component.

The "component (a): 2'-fucosyllactose" used as a utilization component in the present technology is known as a typical component of human milk oligosaccharides (HMOs). Therefore, a commercially available 2'-fucosyllactose (Fucα (1-2) Galβ (1-4) Glc) may be used, or it may also be prepared from milk or obtained by a known organic synthesis, enzyme treatment, or the like. In addition, it is also possible to use milk (e.g., human milk, powdered milks, cow milk, dairy products) containing 2'-fucosyllactose. In addition, it is also possible to use a human milk oligosaccharide containing at least 2'-fucosyllactose, or such a human milk oligosaccharide may be blended with milk (cow milk, powdered milks, etc.) and used (i.e., milk containing a human milk oligosaccharide).

The "components (c): human milk oligosaccharides (hereinafter sometimes referred to as "HMOs")" that can be used as utilization components in the present technology preferably include at least 2'-fucosyllactose and/or lacto-N-tetraose (LNT). Generally, examples of HMOs include 2'-fucosyllactose, 3-fucosyllactose, 2',3-difucosyllactose, 3'-sialyllactose, 6'-sialyllactose, 3-fucosyl-3'-sialyllactose, lacto-N-tetraose, lacto-N-tetraose, lacto-N-fucopentaose lacto-N-fucopentaose II, lacto-N-fucopentaose lacto-N-fucopentaose V, lacto-N-difucosylhexaose I, lacto-N-difucosylhexaose II, lacto-N-sialylpentaose, LSTa, LSTb, and LSTc. The oligosaccharides of these HMOs can each be obtained by a known production method. In the present technology, one or more of these can be used.

As a utilization component in the present technology, it is preferable to use at least one carbohydrate selected from the group consisting of "components (b): xylan, arabinoxylan, arabinan, debranched arabinan, pectin, galactan, pectic galactan, and oligosaccharides derived therefrom" for the purpose of growth promotion; this is because, as a result, the growth of subspecies *longum* having utilization ability therefor can be promoted. In addition, the "components (b)" are preferably water-soluble, and more preferably highly water-soluble.

Of the "components (b)", "xylan, arabinoxylan, arabinan, debranched arabinan, and oligosaccharides derived therefrom" (particularly arabinoxylan and oligosaccharides derived therefrom) are well known as carbohydrates derived from a gramineous plant (polysaccharides, oligosaccharides).

As "arabinoxylan, arabinan, and oligosaccharides derived therefrom" of the "components (b)", commercially available products obtained by processing gramineous plants can be used, or they can also be obtained by extraction from such plants. In addition, the carbohydrates may also be obtained as dietary fibers or the like by processing edible parts of gramineous plants, for example. "Arabinoxylan, arabinan, and oligosaccharides derived therefrom" of the "components (b)" are also present in hull parts (e.g., rice bran, wheat bran, etc.).

Examples of gramineous plants include plants of the genus *Oryza* (rice, such as indica rice and japonica rice, etc.), plants of the genus *Zea* (preferably corn), plants of the genus *Triticum* (preferably wheat), and plants of the genus *Hordeum* (preferably barley), and one or more kinds can be selected from the group consisting thereof.

According to the present technology, suitable selection therefrom can be made according to the ordinary diets of individuals. According to the present technology, particularly in the case of a Japanese dish, it is preferable to select, as a utilization component, a carbohydrate derived from a plant of the genus *Oryza* (preferably an oligosaccharide) or a food containing the same (e.g., a food using rice (specifically boiled rice, brown rice, rice gruel, bread or noodles containing rice flour, etc.)).

Of the "components (b)", "pectin, galactan, pectic galactan, and oligosaccharides derived therefrom" (particularly pectic galactan and oligosaccharides derived therefrom) are known as carbohydrates derived from solanaceous plants or derived from gramineous plants (polysaccharides, oligosaccharides).

In addition, as plants containing "galactan and oligosaccharides derived therefrom" of the "components (b)" of the present technology, solanaceous plants of the genus *Solanum*, legumes, and the like can be mentioned, and one or more kinds can be selected from the group consisting thereof.

For this reason, commercially available products obtained by processing these plants can be used, or extraction from such plants is also possible. For example, carbohydrates derived from plants of the genus *Oryza* (preferably oligosaccharides derived from arabinoxylan), carbohydrates derived from solanaceous plants of the genus Solanum (potatoes, etc.) (preferably oligosaccharides derived from arabinan or derived from pectic galactan), and carbohydrates derived from legumes (preferably oligosaccharides derived from arabinogalactan) can be selected.

Incidentally, unless otherwise noted, "xylan" as used herein means one having a polymer of xylose as the main chain, which may also have other constituent sugars in the side chain or main chain.

In addition, unless otherwise noted, "arabinan" as used herein means one having a polymer of arabinose as the main chain, which may also have other constituent sugars in the side chain or main chain.

In addition, unless otherwise noted, "galactan" as used herein means one having a polymer of galactose as the main chain, which may also have other constituent sugars in the side chain or main chain.

In addition, unless otherwise noted, "pectin" as used herein means a polymer of α1-4-linked galacturonic acid, which may also have other constituent sugars in the side chain or main chain. In addition, "pectin" as used herein includes, regardless of whether the carboxyl groups of galacturonic acid are methyl-esterified, "pectin in a narrow sense" which is methyl-esterified, pectic acid obtained by de-esterifying "pectin in a narrow sense", and "pectic acid" which is not methyl-esterified.

Generally, arabinoxylan is a carbohydrate containing arabinose and xylose as main constituent sugars, and is known as a carbohydrate having a polymer of xylose as the main chain.

The arabinoxylan used in the present technology is preferably configured such that an L-arabinofuranose monosaccharide or an arabino-oligosaccharide thereof is attached as a side chain to the main chain composed of a polymer of β1-4-linked xylose through an α1-3 linkage or α1-2 linkage. Still more preferably, an L-arabinofuranose monosaccharide is attached to the side chain. In addition, the constituent sugar ratio of the arabinoxylan of the present technology is preferably such that the ratio of xylose sugar residues to L-arabinose sugar residues is 5:1 to 4.

In the case of subspecies *longum* having utilization ability for arabinoxylan, it is considered that arabinan and/or xylan can also be used as a utilization component.

In addition, generally, arabinan is a carbohydrate containing arabinose as a main constituent sugar, and is known as a carbohydrate having a polymer of arabinose as the main chain. Examples of arabinans include pectic arabinan and debranched arabinan.

As the arabinan used in the present technology, a carbohydrate having a polymer of α1-5-linked arabinose as the main chain is preferable, and debranched arabinan is still more preferable. Debranched arabinan is obtained by subjecting arabinan having a branched portion to a debranching treatment. As the debranched arabinan, for example, one obtained by debranching pectic arabinan (preferably 1,5-α-L-Arabinan, wherein the proportion of Ara sugar residues is 80% or more) can be mentioned.

In addition, generally, pectic arabinan is known as a carbohydrate composed of an arabinan main chain and pectin . As the pectic arabinan, for example, one in which pectin is attached to C-1 of the reducing end of the main chain arabinan can be mentioned.

In the case of subspecies *longum* having utilization ability for debranched arabinan, it is considered that pectic arabinan can also be used as a utilization component.

Generally, pectic galactan is a carbohydrate composed of a galactan main chain and a galacturonic acid polymer. As the well-known pectic galactan, one in which pectin is attached to C-1 of the reducing end of the main chain galactan can be mentioned.

In the case of subspecies *longum* having utilization ability for pectic galactan, it is considered that pectin and/or galactan can also be used as a utilization component.

Generally, galactan is known as a carbohydrate having galactose as a main constituent sugar and a polymer of galactose as the main chain.

Meanwhile, pectic galactan is known as a carbohydrate having a polymer of β1-4-linked galactose as the main chain.

In addition, galactan is known to be present in soybeans as arabinogalactan. Examples of carbohydrates derived from leguminous plants containing galactan include carbohydrates derived from lupine beans and carbohydrates derived from soybeans. Examples of soybean-derived carbohydrates include processed soybean products (e.g., tofu, soy milk, etc.), fermented soybean products (e.g., miso, soy sauce, natto, etc.), and carbohydrates derived therefrom.

<Composition for Use in Growth Promotion>

Thus, the "component (a): 2'-fucosyllactose" of the present technology has growth promoting action on the subspecies *longum* of the present technology. When the "component (a)" is used further in combination with at least one carbohydrate selected from the group consisting of the components (b): "xylan, arabinoxylan, arabinan, debranched arabinan, pectin, galactan, pectic galactan, and oligosaccharides derived therefrom" and the components (c): "HMOs" (hereinafter also referred to as "combination of the components"), the growth promoting action on the subspecies *longum* of the present technology is more favorably achieved. These components can be used as components for the growth promoting action on the subspecies *longum* of the present technology.

For this reason, the "component (a)" or the "combination of the components" can also be used as a component for promoting the growth of the subspecies *longum* of the present technology.

The "component (a)" or the "combination of the components" can be present as an active ingredient in a composition for use in promoting the growth of the subspecies *longum* of the present technology (hereinafter sometimes referred to as "composition for growth promotion"), and can also be used in products for a wide range of intended uses, including pharmaceuticals, foods and beverages, animal feeds, and the like. These products can be produced suitably using optional components suitable for each intended use by a known production method suitable for each intended use.

In addition, the "component (a)" or the "combination of the components" can be directly used as it is for the purpose of growth promotion of the present technology, or can also be mixed with a physiologically, pharmaceutically, or food acceptable ordinary carrier, diluent, or the like and used.

In addition, the "component (a)" or the "combination of the components" can be used for the production of these various preparations, various formulations, and the like. In addition, the "component (a)" or the "combination of the components" of the present technology can also be used as a composition for use in a method for promoting the growth of the subspecies *longum* of the present technology or for use in promoting the growth (preferably a prebiotic composition).

In addition, in the composition for growth promotion of the present technology, the amount used or content of the "component (a): 2'-fucosyllactose" is preferably 1 to 1,000,000 parts by mass, more preferably 10 to 10,000 parts by mass, per 100 parts by mass of bacteria.

In addition, in the composition for growth promotion of the present technology, the amount used or content of the "at least one carbohydrate selected from the components (b)" is preferably 1 to 1,000,000 parts by mass, more preferably 10 to 10,000 parts by mass, per 100 parts by mass of bacteria.

In addition, in the case where the composition for promoting the growth of the subspecies *longum* of the present technology is a combination of the "component (a)" and the "at least one carbohydrate selected from the components (b)", they can be mixed or used as separate composition kits.

The composition for growth promotion of the present technology described above promotes the growth of the subspecies *longum* of the present technology. Therefore, the composition for growth promotion of the present technology can be used as a prebiotic composition. Use of the composition for growth promotion is expected to have probiotic effects beneficial to human health caused by the subspecies *longum* of the present technology, such as intestinal regulation action, mineral absorption promoting action, and preventing/alleviating action on inflammatory bowel diseases.

In addition, when the composition for growth promotion of the present technology is ingested, growth promoting action on lactic acid bacteria/bifidus bacteria other than the subspecies *longum* of the present technology can also be expected. Thus, the composition can be used as a prebiotic composition for lactic acid bacteria/bifidus bacteria.

It is possible to use a growth promoting component for lactic acid bacteria/bifidus bacteria other than the subspecies *longum* of the present technology. Known examples of such growth promoting components for lactic acid bacteria/bifidus bacteria include carbohydrates such as oligosaccharides (e.g., galactooligosaccharides, fructooligosaccharides, soybean oligosaccharides, milk oligosaccharides (preferably human milk oligosaccharides (HMOs)), xylooligosaccharides, isomaltooligosaccharides, raffinose, lactulose, coffee mannooligosaccharides, gluconic acid, etc.) and dietary fibers (polydextrose, inulin, etc.), and one or more kinds can be selected therefrom.

For this reason, it is preferable that such a growth promoting component for lactic acid bacteria/bifidus bacteria is present as an optional component in the prebiotic composition of the present technology.

Then, the prebiotic composition of the present technology can promote the growth of the subspecies *longum* of the present technology and other lactic acid bacteria/bifidus bacteria. As a result of this, probiotic effects such as intestinal regulation action, mineral absorption promoting action, and preventing/alleviating action on inflammatory bowel diseases can also be more favorably expected.

In addition, various actions of human milk oligosaccharides (HMOs), for example, preventing/alleviating action on allergies, lactose intolerance alleviating action, immunity improving action, protecting action against infection, cerebral nervous system forming action, cerebral nervous system activating action, and the like, are known (Reference 3: Biological significance of human milk oligosaccharides; Milk Science Vol. 56, No. 4 (2008) pp. 155-176). Accordingly, the composition for growth promotion of the present technology can also be expected to have probiotic effects such as preventing/alleviating action on allergic symptoms, lactose intolerance alleviating action, immunity improving action, protecting action against infection, cerebral nervous system forming action, and cerebral nervous system activating action.

<Composition>

The present technology can also provide a composition containing the subspecies *longum* of the present technology. The meaning of the composition of the present technology includes a food or beverage composition, a pharmaceutical composition, an animal feed composition, and the like. In addition, the composition of the present technology is preferably a probiotic composition.

As described above, the subspecies *longum* of the present technology has utilization ability for "2'-fucosyllactose". It is preferable that the subspecies longum of the present technology is further characterized by having utilization ability for "at least one carbohydrate selected from the group consisting of arabinoxylan, arabinan, and pectic galactan" (preferably an oligosaccharide).

Therefore, it is preferable that a utilization component on which the growth of the subspecies *longum* of the present technology can be promoted is further used in the composition containing the subspecies *longum* of the present technology.

The subspecies *longum* of the present technology can more favorably grow in the intestine when ingested at the same time as or separately from a utilization component of the "component (a)" (preferably the "combination of the components") or a food or beverage containing the utilization component. Like this, when a utilization component (i.e., a component for growth promotion) is present, probiotic effects can also be still more favorably expected.

The subspecies *longum* of the present technology may be used for humans or non-human animals (preferably mammals), which are application subjects. Humans and pets are preferable, and humans are more preferable.

Further, those to whom the present technology is to be applied are not particularly limited as long as they desire probiotic effects, and examples thereof include babies, infants, children, adults, healthy people, middle-aged and older people, elderly people, and those with poor intestinal environment. Among them, the present technology is preferably used for babies, for adults, and for elderly people.

The composition containing the subspecies longum of the present technology allows the subspecies *longum* of the present technology to grow in the intestine in a range of diets from those for babies and infants to those for adults, and thus can be expected to have probiotic effects across a wide range of age groups. As a result, for example, improvement in the intestinal environment, intestinal regulation action, mineral absorption promoting action, preventing/alleviating action on inflammatory bowel diseases, and the like can also be expected.

Because the composition containing the subspecies *longum* of the present technology can be expected to have probiotic effects, for example, the prevention, alleviation, or treatment of diseases or symptoms described above, such as allergic symptoms, immune dysfunction, infectious diseases, and nervous system diseases, can be expected. In addition, the composition containing the subspecies *longum* of the present technology can also be expected to have the above preventing action on allergic symptoms, lactose intolerance alleviating action, immunity improving action, protecting action against infection, cerebral nervous system forming action, cerebral nervous system activating action, and the like (Reference 2 and Reference 3).

In addition, the present technology can also be used in or applied to a nursery composition containing a human milk oligosaccharide (HMO) (preferably a baby milk). The nursery composition of the present technology can also be expected to have preventing action on allergic symptoms, lactose intolerance alleviating action, immunity improving action, protecting action against infection, cerebral nervous system forming action, cerebral nervous system activating action, and the like.

In addition, the subspecies *longum* used in the present technology is human-derived, and thus has less side effects and is highly safe. Therefore, continuous ingestion for a long period of time is also possible.

Then, the present technology can also be effectively used for symptoms or diseases that can be prevented, alleviated, or treated by probiotics.

The subspecies *longum* of the present technology can be directly used, or can also be mixed with a physiologically, pharmaceutically, or food acceptable ordinary carrier, diluent, or the like and used.

Therefore, the subspecies *longum* of the present technology can also be present as an active ingredient in a probiotic composition, and, because of its high safety, can also be used in products for a wide range of intended uses, including pharmaceuticals, foods and beverages, animal feeds and the like. These products can be produced suitably using optional components suitable for each intended use by a known production method suitable for each intended use.

In addition, the subspecies *longum* of the present technology can be used for the production of these various formulations or various compositions. In addition, the present technology can also be used as subspecies *longum* for probiotics.

The composition of the present technology contains at least the subspecies *longum* of the present technology, and preferably further contains the growth promoting component described above.

The composition of the present technology preferably contains the "component (a): 2'-fucosyllactose".

Still more preferably, besides "the component (a)", the composition further contains "at least one carbohydrate selected from the group consisting of the components (b): xylan, arabinoxylan, arabinan, debranched arabinan, pectin, galactan, pectic galactan, and oligosaccharides derived therefrom". Among them, it is preferable that at least arabinoxylan and/or pectic galactan is present.

In addition, besides "the component (a)", "at least one carbohydrate selected from the group consisting of arabinoxylan, arabinan, pectic galactan, and oligosaccharides derived therefrom" of "the components (b)" may further be present.

In addition, besides "the above component (a)", the composition of the present technology preferably further contains at least a carbohydrate derived from a gramineous plant and/or a carbohydrate derived from a solanaceous plant.

In addition, the composition containing the subspecies *longum* of the present technology and the composition for promoting the growth of the subspecies *longum* of the present technology can also be used as a mixed composition or as separate composition kits. In addition, the composition for growth promotion of the present technology can also be present as a component of a probiotic composition and used.

The administration or ingestion of the subspecies *longum* of the present technology is preferably continued for at least one week, more preferably continued for at least four weeks, and desirably continued every day.

Because the subspecies *longum* of the present technology is highly safe, the amount used is not particularly limited, but is, for example, preferably $1\times10^6$ to $1\times10^{12}$ CFU/kg body weight/day, more preferably $1\times10^7$ to $1\times10^{11}$ CFU/kg body weight/day, and still more preferably $1\times10^8$ to $1\times10^{10}$ CFU/kg body weight/day. Alternatively, the amount used (dosage) per individual (body weight) is preferably $10^7$ to $10^{14}$ CFU/day, more preferably $10^8$ to $10^{13}$ CFU/day, and still more preferably $10^9$ to $10^{12}$ CFU/day.

In addition, the amount used of the subspecies longum of the present technology is preferably 0.01 to 100 mL/kg body weight/day, and more preferably 0.1 to 10 mL/kg body weight/day.

Incidentally, in the present technology, CFU stands for Colony Forming Unit and represents colony forming units.

In the case where the bacteria are killed bacteria, CFU can be replaced with the number of cells.

In addition, the present technology may be used for therapeutic purposes or may also be used for non-therapeutic purposes.

"Non-therapeutic purpose" is a concept that does not include a medical practice, that is, a practice of therapeutically treating a human body. For example, health promotion, cosmetic treatments, and the like can be mentioned.

"Alleviation" means to change the disease, symptom, or condition for the better; to prevent or delay the deterioration of the disease, symptom, or condition; or to reverse, prevent, or delay the progress of the disease or symptom.

"Prevention" means to prevent or delay the onset of the disease or symptom in the application subject, or to reduce the risk of onset of the disease or symptom in the application subject.

<Pharmaceutical Composition>

Further, the composition of the present technology can be used as a pharmaceutical composition. As a result, probiotic effects can be expected.

The pharmaceutical composition of the present technology is not particularly limited as long as it contains the subspecies *longum* of the present technology. The pharmaceutical composition can be used also as a composition for intestinal regulation containing the subspecies *longum* of the present technology, for example.

As the pharmaceutical composition of the present technology, the subspecies *longum* of the present technology may be directly used, or may also be formulated with a physiologically acceptable liquid or solid pharmaceutical carrier and used.

In addition, the pharmaceutical composition of the present technology contains, as an active ingredient, the subspecies *longum* of the present technology which can be obtained from the human intestine as an oral composition component, and thus can be administered with security even to patients with various diseases. In addition, because *Bifidobacterium* exist also in the intestines of animals, the present technology is expected to be less likely to cause side effects even when administered continuously for a long period of time. In addition, *Bifidobacterium* can be safely administered even to babies, infants, and children. Therefore, the present technology is also preferable for preventing, alleviating, and/or treating diseases or their symptoms in babies, infants, or children.

The dosage form of the pharmaceutical composition of the present technology is not particularly limited, and specific examples thereof include tablets, pills, powders, solutions, suspensions, emulsions, granules, capsules, syrups, suppositories, injections, ointments, patches, eye drops, and nasal drops. In addition, for formulation, additives ordinarily used as pharmaceutical carriers, such as diluents, binders, disintegrators, lubricants, stabilizers, flavoring agents, diluents, surfactants, and solvents for injection, can be used.

In addition, for formulation, in the pharmaceutical composition according to the present technology, components usually used for formulation, such as diluents, pH adjusters, colorants, and corrigents, can be used. In addition, unless the effects of the invention are impaired, in the pharmaceutical composition according to the present technology, components effective in preventing, alleviating, and/or treating muscular diseases or muscle atrophy-associated diseases now known or later discovered, or their symptoms, can also be used.

In addition, formulation can be suitably performed by a known method according to the dosage form. For formulation, the composition may also be suitably formulated with a pharmaceutical carrier.

The content of the subspecies *longum* of the present technology in the pharmaceutical composition of the present technology is suitably set according to the dosage form, the usage, the age and sex of the patient, the kind of disease, the degree of disease, other conditions, and the like, but is usually preferably within a range of $1\times10^6$ to $1\times10^{12}$ cfu/g or $1\times10^6$ to $1\times10^{12}$ cfu/mL, and more preferably within a range of $1\times10^7$ to $1\times10^{11}$ cfu/g or $1\times10^7$ to $1\times10^{11}$ cfu/mL. In the case where bacteria of the subspecies *longum* of the present technology are killed bacteria, cfu/g or cfu/mL can be replaced with the number of cells/g or the number of cells/mL.

The amount used of the subspecies *longum* of the present technology is suitably set according to the dosage form, the usage, the age and sex of the patient, the kind of disease, the degree of disease, other conditions, and the like, but is usually preferably within a range of $1\times10^6$ to $1\times10^{12}$ cfu/g or $1\times10^6$ to $1\times10^{12}$ cfu/mL, and more preferably within a range of $1\times10^7$ to $1\times10^{11}$ cfu/g or $1\times10^7$ to $1\times10^{11}$ cfu/mL. In the case where bacteria of the subspecies *longum* of the present technology are killed bacteria, cfu/g or cfu/mL can be replaced with the number of cells/g or the number of cells/mL.

The timing of administration of the pharmaceutical composition of the present technology is not particularly limited. According to the method for treating the target symptom or disease, the timing of administration can be suitably selected. In addition, the pharmaceutical composition may be administered prophylactically or may also be used for maintenance therapy. In addition, it is preferable that the dosage form is determined according to the formulation form, the age and sex of the patient, other conditions, the degree of patient's symptoms, and the like. Incidentally, in any case, the pharmaceutical composition of the present technology can be administered once or in several portions a day, and may also be administered once in several days or several weeks.

<Food or Beverage Composition>

Further, the composition of the present technology can be used as a food or beverage composition. As a result, probiotic effects can be expected.

The food or beverage composition of the present technology may be produced by adding the subspecies *longum* of the present technology to a known food or beverage, or can also be produced by mixing the subspecies *longum* of the present technology in raw materials for a food or beverage and obtained as a novel food or beverage composition.

The food or beverage composition of the present technology is not particularly limited as long as it contains the subspecies *longum* of the present technology. Examples of food or beverage compositions include beverages such as soft drinks, carbonated beverages, nutritional beverages, fruit juice beverages, and lactic acid bacteria beverages (including liquid concentrates and preparation powders of these beverages); frozen desserts such as ice cream, sherbet, and shaved ice; confectionaries such as candies, chewing gums, candies, gums, chocolates, tablet confectioneries, snack confectioneries, biscuits, jellies, jams, creams, and baked confectioneries; dairy products such as processed milks, milk beverages, fermented milks, yogurt drinks, and butter; bread; enteral foods, liquid foods such as rice gruel, baby foods, nursery milks (e.g., baby milks, etc.), sports beverages; and other functional foods. In addition, the food or beverage may also be a supplement, such as a tablet-shaped supplement, for example. In the case where the food or beverage is a supplement, the subspecies *longum* of the present technology can be ingested without being affected by other foods in terms of the daily food intake and calorie intake.

An example of a more preferred embodiment of the present technology is baby milk (e.g., an infant formula, etc.). The "baby milk" preferably refers to a food intended for a specific nutritional use for babies 4 to 6 months old or 4 to 12 months old, which by itself satisfies the nutritional requirements of babies and infants. Such a composition may contain, for example, one or more probiotic *Bifidobacterium*; prebiotics such as human milk oligosaccharides, fructooligosaccharides, and galactooligosaccharides; proteins derived from casein, soybean, whey, and skimmed milk; carbohydrates such as lactose, saccharose, maltodextrin, starch, and mixtures thereof; lipids (e.g., palm olein, sunflower oil, sunflower oil); and vitamins, minerals, and the like essential for everyday foods. One or more kinds can be selected from these groups.

In addition, unless the effects of the invention are impaired, in the food or beverage composition in the present technology, a component having probiotic effects or a component that aids probiotic effects, now known or later discovered, can be used. For example, the food or beverage composition in the present technology can be prepared by combining, with the subspecies *longum* of the present technology, the following components: various proteins such as whey protein, casein protein, soybean protein, and pea protein, as well as mixtures and breakdown products thereof; amino acids such as leucine, valine, isoleucine, and glutamine; vitamins such as vitamin B6 and vitamin C; creatine; citric acid; fish oil; etc.

In addition, the food or beverage composition defined in the present technology can be provided/sold as a food or beverage with a label stating the intended use such as a probiotic use (including health uses). In addition, it can be provided/sold with a label stating, as subjects to ingest the food or beverage, "those who like Japanese dishes", "those who desire a life with Bifidobacterium", "those who want to improve the intestinal environment", "those who want to regulate the stomach conditions", "those who want to form an excellent intestinal environment", and the like.

"Labeling" includes all acts for making consumers aware of the above intended use. As long as the expression allows consumers to assume or infer the intended use, all such acts fall within the "labeling" of the invention regardless of the purpose of the label, the content of the label, the object/medium to be labeled, and the like.

In addition, it is preferable that "labeling" is performed with an expression that allows consumers to directly recognize the intended use. Specific examples thereof are the following acts: a food- or beverage-related product stating the intended use thereon or on the package thereof is transferred, delivered, displayed for transfer or delivery, or imported; the intended use is described in an advertisement, price list, or transaction document related to the product and displayed or distributed, or the intended use is described in information having such contents and provided through an electromagnetic means (Internet, etc.); and the like.

Meanwhile, with respect to the content of the label, it is preferable that the label has been approved by the government or the like (e.g., a label that has been approved based on systems established by the government and attached in a mode in accordance with the approval, etc.). In addition, it is preferable that such a content of the label is attached to packages, containers, catalogs, pamphlets, POPs and like advertising materials at the sales location, or other documents.

In addition, "labeling" also includes labeling for health foods, functional foods, enteral foods, special purpose foods, foods with health claims, foods for specified health uses, foods with nutrient function claims, foods with function claims, quasi drugs, and the like. Among them, in particular, labels approved by the Consumer Affairs Agency, such as labels approved based on a system concerning foods for specified health uses, foods with nutrient function claims, or foods with function claims or on a similar system, can be mentioned. Specific examples thereof include labels for foods for specified health uses, labels for qualified foods for specified health uses, labels to inform that the body structure or function may be affected, labels to show disease risk reduction, and labels to show evidence-based functionality. More specifically, typical examples are labels for foods for specified health uses (particularly health use claims) under Cabinet Office Ordinance on Permission for Special Use Claims, etc., prescribed in Health Promotion Act (Aug. 31, 2009; Cabinet Office Order No. 57) and similar labels.

The content of the subspecies *longum* of the present technology in the food or beverage composition of the present technology is suitably set according the mode of the food or beverage composition, but is usually, in a food or beverage, preferably within a range of $1 \times 10^6$ to $1 \times 10^{12}$ cfu/g or $1 \times 10^6$ to $1 \times 10^{12}$ cfu/mL, and more preferably within a range of $1 \times 10^7$ to $1 \times 10^{11}$ cfu/g or $1 \times 10^7$ to $1 \times 10^{11}$ cfu/mL.

The amount used of the subspecies *longum* of the present technology is suitably set according the mode of the food or beverage composition, but is usually, in a food or beverage, preferably within a range of $1 \times 10^6$ to $1 \times 10^{12}$ cfu/g or $1 \times 10^6$ to $1 \times 10^{12}$ cfu/mL, and more preferably within a range of $1 \times 10^7$ to $1 \times 10^{11}$ cfu/g or $1 \times 10^7$ to $1 \times 10^{11}$ cfu/mL.

The food or beverage of the present technology can be produced by adding the subspecies *longum* of the present technology to raw materials for a food or beverage composition, and can be produced in the same manner as for ordinary food or beverage compositions, except for adding the subspecies *longum* of the present technology.

Further, the composition for growth promotion described above may be suitably added, and, as the composition for growth promotion, a food that serves as the origin of the composition for growth promotion may also be used, for example.

As raw materials for a food or beverage, raw materials used for ordinary beverages and foods can be used. However, considering the growth promoting component for the subspecies *longum* of the present technology, raw materials for Japanese dishes are preferable.

In addition, according to the purpose, the subspecies *longum* of the present technology can also be used together with other "*Bifidobacterium* and/or lactic acid bacteria" for use in foods and beverages.

The food or beverage composition of the present technology also includes raw materials for producing the food or beverage composition, food additives, and the like added to a food or beverage in the course of or after the production of the food or beverage composition.

In the production of the food or beverage of the present technology, the subspecies *longum* of the present technology may be added in any step of the production of the food or beverage composition. For example, as an example, generally, it may be added in the step of adding *Bifidobacterium*.

The produced food or beverage can be orally ingested.

Examples of foods and beverages containing the subspecies *longum* of the present technology include Japanese dishes such as rice gruel, baby foods, liquid foods (preferably for elderly people, etc.), baby milks, lactic acid bacteria beverages, and fermented milks.

When the food or beverage of the present technology is a Japanese dish having fluidity, such as rice gruel, such a food or beverage can be used as a baby food and also as a liquid food for elderly people. Even in the case of an elderly person who is restricted from eating Japanese dishes, he/she can eat a Japanese dish as rice gruel or the like, which can lead to improved diets. Like this, according to the present technology, while improving the quality of diets, and while expecting probiotic effects, the family can gather and eat same foods.

In addition, there is a possibility of utilization of even fermented soybean-derived carbohydrates, which suggests that the Japanese dishes may also be miso soup, natto, and the like.

The present technology can also be configured as follows.

[1] *Bifidobacterium longum* subspecies *longum* NITE BP-02568 and/or *Bifidobacterium longum* subspecies *longum* NITE BP-02569.

[2] *Bifidobacterium longum* subspecies *longum*, having utilization ability for 2'-fucosyllactose.

[3] Bacteria further having utilization ability for at least one carbohydrate selected from the group consisting of arabinoxylan, arabinan, and pectic galactan.

The bacteria are more preferably *Bifidobacterium longum* subspecies *longum* NITE BP-02568 and/or *Bifidobacterium longum* subspecies *longum* NITE BP-02569.

[4] A composition containing the bacteria according to any one of the above [1] to [3] or use of the bacteria according to any one of the above [1] to [3] in a composition. The composition is preferably a composition for pharmaceuticals or a food or beverage composition.

[5] The composition according to the above [4] or the use of bacteria in a composition according to the above [4], wherein the composition is a probiotic composition.

[6] The composition according to the above [4] or [5] or the use of bacteria in a composition according to the above [4] or [5], wherein the composition is used at least for babies and infants, for adults, or for elderly people.

[7] The composition according to any one of the above [4] to [6] or the use of bacteria in a composition according to any one of the above [4] to [6], wherein the composition is a composition used for intestinal regulation or for foods and beverages.

[8] The composition according to any one of the above [4] to [7] or the use of bacteria in a composition according to any one of the above [4] to [7], wherein the composition further contains 2'-fucosyllactose or a human milk oligosaccharide (HMO).

[9] The composition according to the above [8] or the use of bacteria in a composition according to the above [8], wherein the composition further contains at least one carbohydrate selected from the group consisting of arabinoxylan, xylan, arabinan, pectic galactan, pectin, galactan, and oligosaccharides derived therefrom.

The composition preferably further contains lacto-N-tetraose as the carbohydrate.

Among them, as a more preferred carbohydrate, at least one carbohydrate selected from the group consisting of arabinoxylan, arabinan, pectic galactan, and oligosaccharides derived therefrom is present. The arabinan is preferably debranched arabinan.

[10] The composition according to the above [8] or [9] or the use of bacteria in a composition according to the above [8] or [9], wherein the composition further contains at least a carbohydrate derived from a gramineous plant, a carbohydrate derived from a solanaceous plant, or a carbohydrate derived from legumes.

Among them, a more preferred carbohydrate is at least a carbohydrate derived from a gramineous plant or a carbohydrate derived from a solanaceous plant.

[11] Use of the bacteria according to any one of the above [1] to [3] in the production of a composition. The composition is preferably the composition according to any one of the above [4] to [10]. Alternatively, the composition is preferably a composition for pharmaceuticals or a food or beverage composition (more preferably a baby milk).

[12] The bacteria according to anyone of the above [1] to [3] for use in a composition. The composition is preferably the composition according to any one of the above [4] to [10]. Alternatively, the composition is preferably a composition for pharmaceuticals or a food or beverage composition (more preferably a baby milk).

[13] A method for preventing, alleviating, or treating a disease, symptom, or condition by probiotics, including administering the bacteria according to any one of the above [1] to [3]. The method is preferably a method for preventing, alleviating, or treating allergic symptoms, immune dysfunction, infectious diseases, or nervous system diseases. Apreventing, alleviating, ortreatingmethod. The method is preferably a method for health promotion, diet improvement, improvement in the intestinal environment, or intestinal infection prevention or treatment.

[14] A prebiotic composition for use in promoting the growth of *Bifidobacterium longum* subspecies *longum*, the composition containing 2'-fucosyllactose or a human milk oligosaccharide (HMO).

The bacteria according to any one of the above [1] to [3] are preferable.

Combined use of the 2'-fucosyllactose or human milk oligosaccharide (HMO) and the carbohydrate according to the above [9] or [10] is still more preferable.

[15] Use of 2'-fucosyllactose or a human milk oligosaccharide (HMO) in a prebiotic composition for promoting the growth of *Bifidobacterium longum* subspecies *longum* containing 2'-fucosyllactose or a human milk oligosaccharide (HMO).

The bacteria according to any one of the above [1] to [3] are preferable. Combined use of the 2'-fucosyllactose or human milk oligosaccharide (HMO) and the carbohydrate according to the above [9] or [10] is still more preferable.

[16] 2'-Fucosyllactose or a human milk oligosaccharide (HMO) for promoting the growth of *Bifidobacterium longum* subspecies *longum*.

The bacteria according to any one of the above [1] to [3] are preferable. Combined use of the 2'-fucosyllactose or human milk oligosaccharide (HMO) and the carbohydrate according to the above [9] or [10] is still more preferable.

[17] Use of 2'-fucosyllactose or a human milk oligosaccharide (HMO) for producing a prebiotic composition for promoting the growth of *Bifidobacterium longum* subspecies *longum*.

The bacteria according to any one of the above [1] to [3] are preferable. Combined use of the 2'-fucosyllactose or human milk oligosaccharide (HMO) and the carbohydrate according to the above [9] or [10] is still more preferable.

[18] A method for promoting the growth of *Bifidobacterium longum* subspecies longum, using 2'-fucosyllactose or a human milk oligosaccharide (HMO).

The bacteria according to any one of the above [1] to [3] are preferable. Combined use of the 2'-fucosyllactose or human milk oligosaccharide (HMO) and the carbohydrate according to the above [9] or [10] is still more preferable.

[19] A method for producing a composition containing bacteria that are classified as *Bifidobacterium longum* subspecies *longum* and have utilization ability for 2'-fucosyllactose or a human milk oligosaccharide (HMO).

The method is preferably a method for producing a composition containing 2'-fucosyllactose or a human milk oligosaccharide (HMO). In addition, the composition is preferably a composition for pharmaceuticals or a composition for foods and beverages. In addition, it is preferably a prebiotic composition, a liquid food, a baby food, a composition for babies and infants (preferably a baby milk), a composition for adults, or a composition for elderly people.

In addition, it is preferably a composition kit composed of a plurality of articles selected from fermented compositions, non-fermented compositions, beneficial bacteria-containing compositions, and foods and beverages. Combined use of the 2'-fucosyllactose or human milk oligosaccharide (HMO) and the carbohydrate according to the above [9] or [10] is still more preferable. In addition, the bacteria according to any one of the above [1] to [3] are preferable.

EXAMPLES

Hereinafter, the invention will be explained using examples, comparative examples, etc., but the invention is not limited to these examples.

Test Example 1

Acquisition of *Bifidobacterium longum* Subsp. *longum* Strain Group

Samples collected from feces of various age groups in Japan were diluted with a sterilized 0.85% physiological saline solution, applied to Difco™ Lactobacilli MRS Agar (Becton Deckinson and Company) of the following composition, and anaerobically cultured at 30° C.

[Difco™ Lactobacilli MRS Agar]

Proteose peptone No. 3, 10.0 g; beef extract, 10.0 g; yeast extract, 5.0 g; dextrose, 20.0 g; polysorbate 80, 1.0 g; ammonium citrate, 2.0 g; sodium acetate, 5.0 g; magnesium sulfate, 0.1 g; manganese sulfate, 0.05 g; dipotassium phosphate, 2.0 g; agar, 15.0 g; purified water, 1,000 mL; pH 6.5±0.2, were sterilized at 121° C. for 15 minutes and then poured into petri dishes to prepare plates.

Then, from the obtained colonies, the smear was observed under a microscope to pick bacteria that were Gram-positive bacilli or -variable bacilli. These bacteria were streaked on a BL agar medium (Eiken Chemical Co., Ltd.), and anaerobic culture was repeated in the same manner as above, thereby giving pure isolated strains.

[BL Agar Medium]

Meat extract, 3.0 g; liver extract, 5.0 g; yeast extract, 5.0 g; peptone, 15.0 g; soy peptone, 3.0 g; soluble starch, 0.5 g; glucose, 10.0 g; dipotassium phosphate, 1.0 g; monopotassium phosphate, 1.0 g; magnesium sulfate, 0.2 g; sodium chloride, 0.01 g; manganese sulfate, 0.00674 g; L-cysteine hydrochloride, 0.5 g; ferrous sulfide, 0.01 g; polysorbate 80, 1.0 g; agar, 15.0 g; purified water, 1,000 mL; pH 7.2±0.2, were sterilized at 121° C. for 15 minutes, then cooled to 50° C. followed by adding 5% (V/V) sterile defibrinated horse blood, and poured into petri dishes to prepare plates.

Further, from the group of pure isolated strains (base sequences of the genomic DNAs of the strains), using the Bacterial 16sRNA DNA PCR kit manufactured by Takara Bio Inc., sample DNA solutions for use in PCR were prepared according to the protocols. Using such a sample DNA solution, the 16SrRNA gene was amplified by PCR to give a DNA amplification product, and the 16SrRNA gene sequences of these strains were determined therefrom.

Based on the base sequence information, on the International Base Sequence Database (Genbank) of NCBI (National Center for Biotechnology Information), homology search for the full length of each 16S ribosomal RNA (SrRNA) gene sequence was performed with BLAST (Basic Local Alignment Search Tool, blast.ncbi.nlm.nih.gov/Blast.cgi), and, as a result, bacteria that showed high homology with *Bifidobacterium longum* subsp. *longum* JCM 1217 (98.6% or more) were defined as *Bifidobacterium longum* subsp. *longum* strains. Incidentally, these strains were Gram-positive.

Test Example 2

Acquisition of Subspecies *longum* Having Utilization Ability for 2'-Fucosyllactose Into 1 mL of an MRS (de Man-Rogosa-Sharpe) liquid medium with the sugar source changed to the sugars shown in Table 1 alone, the plurality of *Bifidobacterium longum* subsp. *longum* strains obtained were each inoculated at 1 v/v % and cultured at 37° C. under anaerobic conditions. The turbidity (OD 600) was measured after 24 hours of culture, and the difference after subtracting the turbidity of a control, in which a medium uninoculated with the strain was similarly cultured, was used to determine the presence of utilization and the degree of utilization ability according to the following standards. When the difference in OD 600 from the control was 0.3 or more, the strain was rated as "having excellent utilization", 0.5 or more as "having more excellent utilization", and 0.8 or more as "having extremely excellent utilization". As a reference, *Bifidobacterium longum* subspecies *longum* NITE BP-02497 (Accession No.: NITE BP-02497) classified as *Bifidobacterium longum* subsp. *longum* was used.

(1) LNT (lacto-N-tetraose): Funakoshi Co., Ltd.

(2) 2'-FL (2'-fucosyllactose): Fucα(1-2)Galβ(1-4 Glc): Funakoshi Co., Ltd.

(3) Arabinoxylan (AX) (highly water-soluble): wheat-derived: main chain-4)Xyl β(1-: constituent sugars Ara:Xyl=38:62, glucose, galactose, andmannose<1%: Megazyme, Co. (secure.megazyme.com/Arabinoxylan-Wheat-Flour-Low-Viscosity)

(4) Debranched arabinan (DA) (highly water-soluble): sugar beet-derived: main chain-5)Ara α(1-: constituent sugars 1,5-α-L-Arabinan, Ara:Gal:Rha:GalUA=88:4:2:6, Megazyme, Co. (secure.megazyme.com/Debranched-Arabinan-Sugar-Beet)

(5) PG (Pectic galactan) (highly water-soluble): potato-derived: main chain-4)Gal β(1-: constituent sugars Gal:Ara:Rha:Xyl:GalUA=77:14:3:0.6:5.4, Megazyme, Co. (secure.megazyme.com/Pectic-Galactan-Lupin)

Incidentally, Fuc stands for fucose (also referred to as 6-deoxygalactose), Gal for galactose, Glc for glucose, Ara for arabinose, Xyl for xylose, Rha for rhamnose (also referred to as 6-deoxymannose), and GalUA for galacturonic acid.

The *Bifidobacterium longum* subspecies *longum* NITE BP-02497 strain was internationally deposited as a *Bifido-* bacterium longum MCC0300 (accession No.: NITE BP-02497) strain on Jun. 22, 2017, to National Institute of Technology and Evaluation, NITE Patent Microorganisms Depositary (NPMD) (address: 2-5-8 Kazusakamatari, Kisarazu, Chiba 292-0818, Japan). This strain is available to the public from the above collection.

Strains found to have the above 2'-FL (2'-fucosyllactose) as a result of the above utilization ability are shown in Table 1. That is, two strains were found.

Specifically, *Bifidobacterium longum* subspecies *longum* NITE BP-02568 and *Bifidobacterium longum* subspecies *longum* NITE BP-02569 were observed to have particularly high utilization ability for 2'-FL (fucosyllactose).

These two strains were identified as *Bifidobacterium longum* subsp. *longum* strains as described above, belonging to the same bacterial group. The homology at this time was 99.9% for the *longum* NITE BP-02568 and 99.6% for the *longum* NITE BP-02569.

Unlike generally known *Bifidobacterium longum* subsp. *longum* (see, e.g., Reference 1), these two strains utilize 2'-FL (fucosyllactose). As a result, the presence of a novel bacterial group (a bacterial group having utilization ability for 2'-FL) was found from these two strains. Incidentally, these two strains each had an OD within a range of 0.6 to 0.8, and thus can be regarded as having extremely excellent utilization ability.

Further, these two strains were observed to have high utilization of arabinoxylan (AX), debranched arabinan (DA), or PG (pectic galactan). In addition, these two strains have high utilization ability for LNT (lacto-N-tetraose). However, these two strains were not observed to have utilization ability for sialic acid and dextrin (DE3.5).

These two strains were observed to have particularly high utilization of the following three: 2'-FL (fucosyllactose), arabinoxylan (AX), and PG (pectic galactan). As a result, these two strains were observed to be capable of growing on human milk oligosaccharides and also on carbohydrates derived from gramineous plants or derived from solanaceous plants. Then, it was considered possible to beneficially apply these bacterial groups across a wide range of age groups including babies, infants, and elderly people, and to particularly expect probiotic effects. Further, it was considered possible to provide a composition applying these bacterial groups and also a composition for promoting the growth of these bacterial groups.

TABLE 1

| Strain Name |
| --- |
| Human milk oligosaccharide |
| Gramineous plant-derived carbohydrate |
| Solanaceous plant-derived carbohydrate |

Incidentally, 16SrDNA gene sequences of

*Bifidobacterium longum* subspecies *longum* NITE BP-02568 (accession No.: NITE BP-02568) and *Bifidobacterium longum* subspecies *longum* NITE BP-02569 (accession No.: NITE BP-02569) are shown as SEQ ID NO: 1 in Table 2 and as SEQ ID NO: 2 in Table 3, respectively.

TABLE 2

| 16SrDNA Gene Sequence of MCLON2FL1_NITE |
| --- |
| BP-02568 (SEQ ID NO: 1) (full-length sequence: 1,535 bp) |

TABLE 3

| 16SrDNA Gene Sequence of MCLON2FL2_NITE |
| --- |
| BP-02569 (SEQ ID NO: 2) (full-length sequence: 1,536 bp) |

Production Example 1

At least one of the subspecies *longum* NITE BP-02568 and the subspecies *longum* NITE BP-02569 is added to 3 mL of an MRS liquid medium and anaerobically cultured at 37° C. for 16 hours, and the culture solution is concentrated and lyophilized into a lyophilized powder of the bacteria (bacterial powder). The bacterial powder is uniformly mixed with rice gruel into a composition. The composition is served to elderly people as a liquid food for elderly people. The composition is served every day at breakfast for 1 week such that the intake of bacteria is $1\times10^8$ to $1\times10^{10}$ CFU/kg body weight/day.

The raw material for rice gruel is polished rice, and rice contains arabinoxylan. Therefore, when the liquid food for elderly people of the present technology is continuously ingested by elderly people, an improving effect on the intestinal environment of elderly people can be expected. In addition, when the composition of Production Example 1 is continuously ingested as a rice gruel product by adults in the same manner, an improving effect on the intestinal environment can be expected. Further, the composition of Production Example 1 can also be used as a baby food for babies and infants. When the composition is continuously ingested by babies and infants in the same manner, an excellent intestinal flora forming effect in babies and infants can be expected.

In addition, the raw material for the rice gruel product may be brown rice instead of polished rice. Because brown rice abundantly contains hull components, an improving effect on the internal environment can be more favorably expected from a brown rice gruel product.

Production Example 2

Both the subspecies *longum* NITE BP-02568 and the subspecies *longum* NITE BP-02569 are added to 3 mL of an MRS liquid medium and anaerobically cultured at 37° C. for 16 hours, and the culture solution is concentrated and lyophilized into granules of the bacteria (bacterial powder). The granular bacterial powder is served every day for a week such that the intake of bacteria is $1\times10^8$ to $1\times10^{10}$ CFU/kg body weight/day.

The granular bacterial powder of Production Example 2 is ingested before or after eating Japanese dishes or between meals. As the Japanese dishes, rice serves as a staple food, and processed potatoes (stew, potato salad, croquettes, etc.), for example, are eaten as side dishes. When the dry bacterial powder product of the present technology is ingested together with Japanese dishes, an improving effect on the intestinal environment of adults can be expected.

In addition, the granular bacterial powder of Production Example 2 is blended upon ingesting a powdered milk.

Because the bacteria have utilization ability for 2'-fucosyllactose, they can grow well even in the intestines of babies and infants, and the intestinal environment of babies and infants can be improved.

In addition, because the bacteria have utilization ability for 2'-fucosyllactose and also utilization ability for the components present in Japanese dishes such as rice described above, they can grow well even in the intestines of adults or elderly people, and the intestinal environment of adults or elderly people can be improved.

Production Examples 3 to 5

1,160 g of skimmed milk (manufactured by Morinaga Milk Industry Co., Ltd.), 500 g of desalted whey powder (manufactured by Domo Company), 59 g of lactose (manufactured by Milei GmbH), and 52 g of dextrin (manufactured by Toyo Sugar Refining Co., Ltd.) are dissolved in 5,471 g of water, and mixed with 143 g of a 10% casein solution previously dissolved and deodorized with caustic soda. Further, 240 g of fish oil-containing formulated oil/fat (containing 1.5 g of fish oil manufactured by NOF Corporation per 100 g of oil/fat) and 33 g of salt-free butter (manufactured by Morinaga Milk Industry) are mixed therewith, subjected to a homogenization treatment under a pressure condition of 15 MPa, and then dried into a powdered milk. The subspecies *longum* NITE BP-02568 and/or the subspecies *longum* NITE BP-02569 is blended with this powdered milk and dried, thereby producing a nursery powdered milk containing the subspecies *longum* (Production Example 3).

In addition, it is also possible that before the homogenization treatment, 2'-fucosyllactose is blended in an amount of 10 to 10,000 parts by mass per 100 parts by mass of bacteria assumed, thereby giving a nursery powdered milk containing 2'-fucosyllactose (not containing the bacteria of the present technology) (Production Example 4), or it is also possible that the subspecies *longum* is further blended, thereby giving a nursery powdered milk (containing the bacteria of the present technology) (Production Example 5). In addition, they may also be produced as baby liquid milks.

Because the bacteria of the present technology have utilization ability for 2'-fucosyllactose, they can grow well even in the intestines of babies and infants, and the intestinal environment of babies and infants can be improved. In addition, because a HMO, which is a utilization component, is present, the bacteria of the present technology having utilization ability for 2'-fucosyllactose can grow well, and the advantages of HMOs can also be obtained. In addition, the present technology can also be expected to provide preventing/alleviating action on allergic symptoms, lactose intolerance alleviating action, immunity improving action, protecting action against infection, cerebral nervous system forming action, and cerebral nervous system activating action.

From the above, the subspecies *longum* having utilization ability for 2'-fucosyllactose, a composition containing the subspecies *longum*, and a composition for promoting the growth of the subspecies *longum* can support the growth of *Bifidobacterium* in the intestine, and can also be effectively used for excellent intestinal flora formation, improvement in the intestinal environment, and the like.

Accession Numbers (1) *Bifidobacterium longum* subspecies *longum* NITE BP-02568 (accession No.: NITE BP-02568) (accession date: Nov. 10, 2017), depository: National Institute of Technology and Evaluation, NITE Patent Microorganisms Depositary (NPMD), 2-5-8 Kazusakamatari, Kisarazu, Chiba 292-0818, Japan.

(2) *Bifidobacterium longum* subspecies *longum* NITE BP-02569 (accession No.: NITE BP-02569) (accession date: Nov. 10, 2017), depository: National Institute of Technology and Evaluation, NITE Patent Microorganisms Depositary (NPMD), 2-5-8 Kazusakamatari, Kisarazu, Chiba 292-0818, Japan.

(3) *Bifidobacterium longum* subspecies *longum* NITE BP-02497 (accession No.: NITE BP-02497) (accession date: Jun. 22, 2017), depository: National Institute of Technology and Evaluation, NITE Patent Microorganisms Depositary (NPMD), 2-5-8 Kazusakamatari, Kisarazu, Chiba 292-0818, Japan.

The invention claimed is:

1. A granular bacterial powder of *Bifidobacterium longum* subspecies *longum* NITE BP-02569.

2. The granular bacterial powder of claim 1, wherein said *Bifidobacterium* is able to utilize 2'-fucosyllactose, and wherein said *Bifidobacterium* is further able to utilize a carbohydrate selected from the group consisting of arabinoxylan, arabinan, pectic galactan, and combinations thereof.

3. A method for producing a granular bacterial powder containing microorganisms that are classified as *Bifidobacterium longum* subspecies *longum* and are able to utilize 2'-fucosyllactose, and wherein said bacterium is further able to utilize a carbohydrate selected from the group consisting of arabinoxylan, arabinan, pectic galactan, and combinations thereof; wherein said method comprises:

i) culturing *Bifidobacterium longum* subspecies *longum* NITE BP-02569;

ii) concentrating and lyophilizing the result of said culturing to produce a granular bacterial powder.

* * * * *